United States Patent
Geiger et al.

(10) Patent No.: US 8,862,484 B2
(45) Date of Patent: Oct. 14, 2014

(54) METHOD AND APPARATUS TO SUPPORT EVIDENCE BASED MEDICINE

(75) Inventors: Bernhard Geiger, Cranbury, NJ (US);
Rainer Kuth, Hoechstadt (DE); James G. Reisman, Plainsboro, NJ (US);
Seiichi Tadano, Tokyo (JP)

(73) Assignees: Siemens Aktiengesellschaft, Munich (DE); Olympus Medical Systems Corporation, Tokyo (JP); Siemens Corporate Research, Inc., Princeton, NJ (US)

( * ) Notice: Subject to any disclaimer, the term of this patent is extended or adjusted under 35 U.S.C. 154(b) by 394 days.

(21) Appl. No.: 12/717,310

(22) Filed: Mar. 4, 2010

(65) Prior Publication Data
US 2011/0218919 A1      Sep. 8, 2011

(51) Int. Cl.
| G06Q 10/00 | (2012.01) |
| G06Q 50/00 | (2012.01) |
| A61B 5/00  | (2006.01) |
| H04L 9/00  | (2006.01) |
| A61B 1/00  | (2006.01) |

(52) U.S. Cl.
CPC *A61B 1/00* (2013.01); *G06Q 50/00* (2013.01); *A61B 5/00* (2013.01); *H04L 9/00* (2013.01)
USPC .................................................. 705/2; 705/3

(58) Field of Classification Search
CPC ............................. G06Q 50/22; G06Q 50/24
USPC ......................................................... 705/2, 3
See application file for complete search history.

(56) References Cited

U.S. PATENT DOCUMENTS

| 6,993,402 B2 * | 1/2006 | Klass et al. .................... 700/103 |
| 7,930,191 B1 * | 4/2011 | Rogers ............................... 705/2 |
| 2002/0095585 A1 * | 7/2002 | Scott ............................. 713/185 |
| 2002/0111833 A1 * | 8/2002 | Dick ................................. 705/3 |
| 2002/0112177 A1 * | 8/2002 | Voltmer et al. ................ 713/200 |
| 2003/0120544 A1 | 6/2003 | Gritzbach et al. |
| 2003/0229521 A1 | 12/2003 | Fuchs et al. |
| 2005/0278197 A1 * | 12/2005 | Podczerwinski et al. ......... 705/3 |
| 2009/0024415 A1 * | 1/2009 | Alpert et al. ...................... 705/3 |

OTHER PUBLICATIONS

Meng et al., Wireless Robotic Capsule Endoscopy, Jun. 15-19, 2004.*
James Reisman, Secure Matching of Fingerprint Templates Consisting of a Smart Chip Device and a Scanning Unit, Feb. 14, 2003.

* cited by examiner

*Primary Examiner* — Neha Patel
(74) *Attorney, Agent, or Firm* — Schiff Hardin LLP

(57) ABSTRACT

A method and apparatus for providing reports of medical procedures includes a biometric data recorder to record and transmit biometric data of a patient, the biometric data being transmitted with a medical report of the medical procedure. The medical report and biometric data are transmitted as an encrypted transmission to an information center for storage. The medical reports of steps in the medical procedure for a patient are linked using the biometric data even if performed by different medical service providers. Medical reports of plural patients undergoing the procedure are stored, linked according to patient using the patient biometric data. Reports generated from the linked data anonymously report a given patient's status following the procedure. Statistical reports are generated on plural patients undergoing the procedure, and competing procedures are compared using the statistical reports.

4 Claims, 4 Drawing Sheets

METHOD AND APPARATUS TO SUPPORT EVIDENCE BASED MEDICINE

BACKGROUND OF THE INVENTION

1. Field of the Invention

The present invention relates generally to method, apparatus and business model for collecting evidence of and reporting on patient medical status relating to a medical procedure, and in particular to use of biometric data of patients to link medical reports relating to the medical procedure.

2. Description of the Related Art

New medical procedures offer the potential to improve a patient's quality of life. However, new medical procedures may not be accepted unless evidence can be provided that the procedure has the ability to provide an improvement in the quality of the patient's life. Proof of the benefits of a procedure may be referred to as evidence based medicine.

Over the course of providing treatment to a patient, the patient is often treated by several different medical service providers. In one example, a patient is seen by a screening physician, a home-care physician, a specialist at a local hospital, and then by a specialist at a specialized hospital. Follow-up care may involve one or more of the specialist medical professionals, the patient's personal care physician, or a rehabilitation center. Regular medical care, such as check-ups, may involve other medical service providers. Payment or reimbursement for the medical procedure and for other medical care is provided according to several different models. Some expenses are paid by health insurance, some by employer plans, some by the patient as out-of-pocket expenses, and other by public medical programs, such as Medicare or Medicaid.

Tracking a patient's progress and quality of life through the different medical service providers and payment or reimbursement models has been difficult or impossible. The result is that evidence is lost over the course of the medical procedure and following the procedure that could have been used to evaluate the success or failure of the procedure, or to identify problems or benefits of the procedure.

Published pending patent application US 2003/0229521 A1 of Fuchs et al. provides for acquisition of biometric data before a medical procedure and storing the data as a record. A method for administering patient medical records includes checking in with information of the initial disease or suspicion and a planned new examination.

Any collection of biometric data of a patient must comply with the Biometric Information Privacy Act and other related laws.

Published pending patent application US 2003/0120544 A1 of Gritzbach et al. relates to an incentive system that provides premiums to subscribers to promote objectives.

SUMMARY OF THE INVENTION

The present invention provides a method and apparatus as well as a business model for tracking a patient who is undergoing a medical procedure. Biometric data of the patient is recorded and transmitted with a medical report on the procedure performed on the patient to an information center using encryption. Medical information is collected in the information center from the medical service providers that work with this patient on this procedure and any follow up medical care. Medical information from other patients having this procedure performed is also collected in the information center, along with medical information for other, competing or alternative procedures.

Anonymous reports of the same patient throughout the course of the treatment and the follow-up care are generated using the biometric data as an identity key to group reports from different medical service providers. Statistical reports of multiple patients undergoing a given procedure are generated, also anonymously to the identity of the patients. Comparisons are generated to compare progress of patients undergoing alternative treatments. Evidence based medicine measuring the quality of life of patients undergoing the tracked medical procedures is thereby available.

DETAILED DESCRIPTION OF THE PREFERRED EMBODIMENTS

Figure 1:
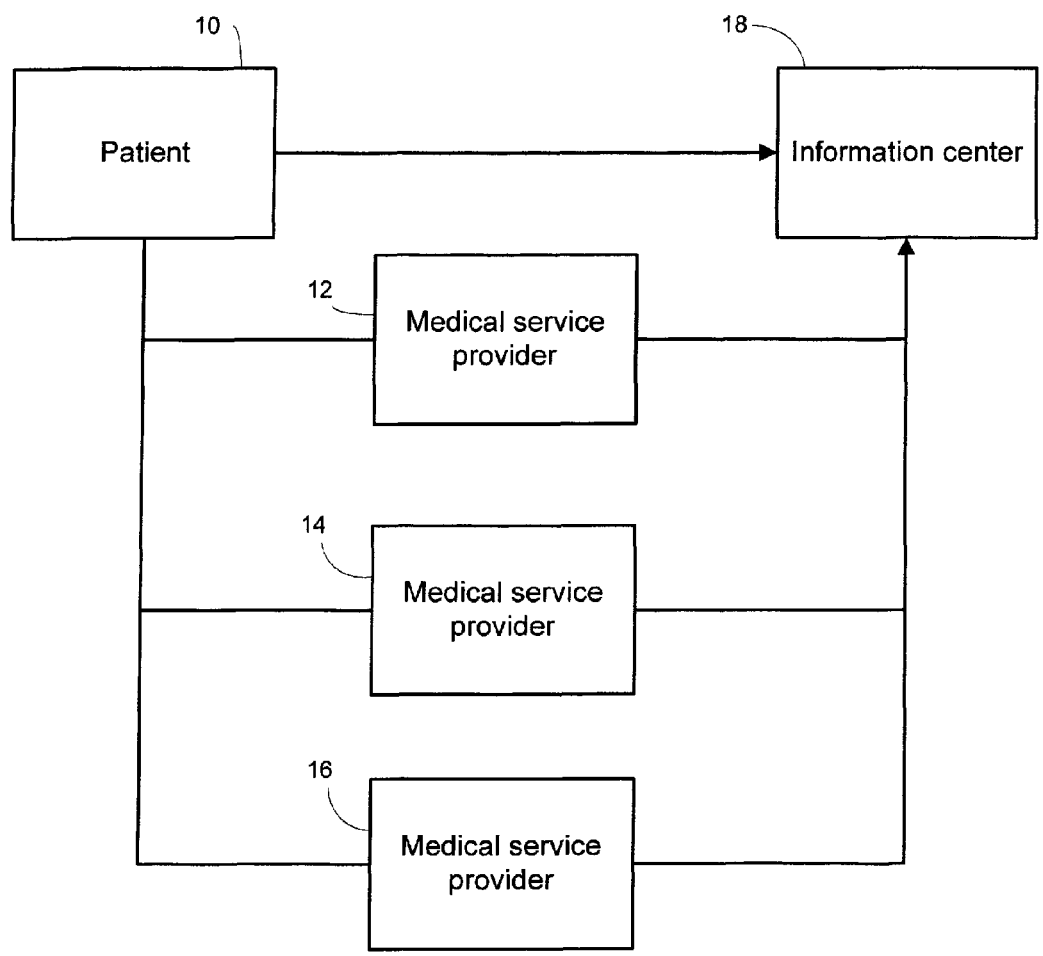
FIG. 1 is a block diagram showing the patient, medical service providers and the information center.

Referring to the drawings, there is shown in FIG. 1 a patient 10 who will receive a medical procedure to diagnose or treat a medical condition. An aspect or step of the medical procedure is performed by a first medical service provider 12. Thereafter or in conjunction therewith a second medical service provider 14 provides another aspect or step of the medical procedure for the patient 10. A third medical service provider 16 provides yet another aspect of the medical procedure for the patient 10. The medical service providers 12, 14 and 16 may be involved in various stages of the medical procedure at different times, or may be providing medical services to the patient 10 simultaneously. Of course, more or fewer medical service providers may be involved in providing the medical procedure to the patient 10.

The medical service providers may be any medical service provider, such as a doctor, nurse, patient care technician, anesthesiologist, radiologist, paramedic or other general medical care provider or specialist, or may be a hospital, clinic, doctor's office, medical imaging facility or other facility or entity. The medical information relating to the procedure being performed for the patient may be reported by the medical personnel or by the medical facility, or may be reported by a medical payment entity such as an insurance company, medical payment center, government payment entity including Medicare or Medicaid, employer medical payment entity or other medical service payer. For purposes of the present method and apparatus, the medical services provider includes any entity involved in providing medical care to the patient including the medical payment facility.

The patient 10 provides information, such as identity information, to an information center 18. The identity information preferably includes biometric information of the patient, although the identity information may include birth date information, procedure date information or other information in addition to or instead of the biometric information. Each of the medical service providers 12, 14 and 16 forwards information on the patient and the procedure to the information center 18. The information sent to the information center 18 preferably includes information on the status of the patient's medical condition and quality of life, particularly with regard to the medical condition that resulted in the procedure being performed on the patient.

Figure 2:
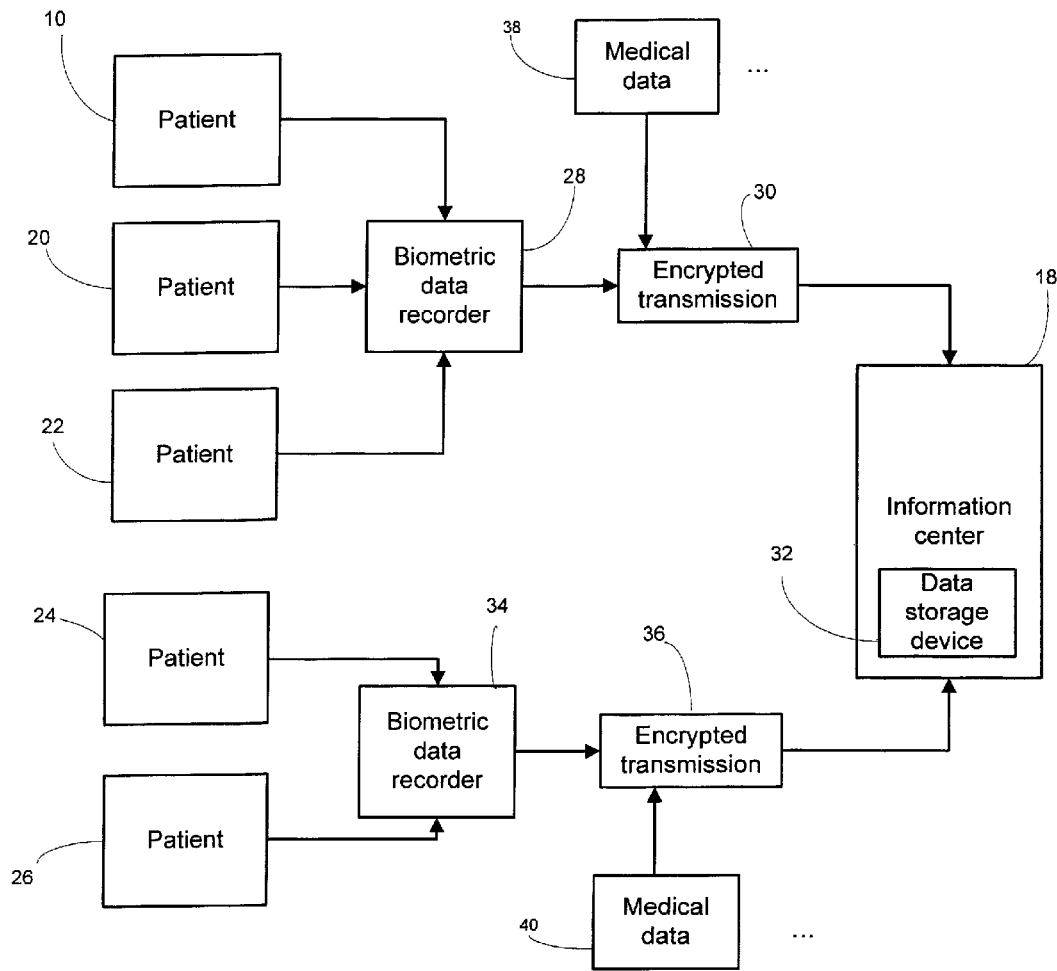
FIG. 2 is a block diagram showing the transmission of biometric data to the information center.

In FIG. 2, the medical procedure is performed on a number of patients 10, 20, 22, 24 and 26, for example. Biometric information of each of the patients 10, 20 and 22 is obtained by a biometric data recorder 28. One example of the biometric information is a fingertip image of the patient's finger which is obtained by a fingerprint reader or hand print reader as the biometric data recorder 28. The biometric data recorder may instead be an iris or retina scanner, voice scanner, face recognition device, DNA reader or other physiological or behavioral trait recorder for other biometric information. The further patient information, including the biometric information of the patient obtained by the biometric data recorder 28, is transmitted via encrypted transmission 30 to the information center 18. The encrypted transmission preferably includes medical information of the patient, and in particular medical information relating to the procedure. The encrypted transmission 30 may be via wireless or wired transmission and may be by transmission of by network connection, including via the Internet, or by any other communication means. The information center 18 receives the patient information and stores it in a data storage device 32. The information center 18 preferably includes one or more computers such as server computers. The data storage device 32 is preferably one or more computer readable media, such as a computer hard drive, solid state memory, optical memory, magnetic media or other data storage device or group of storage devices.

In some embodiments, the patient information sent to the information center 18 is anonymous as to the patient with the exception of the biometric data from the biometric recording device. For example, the information center 18 receives a medical report of a procedure including such information as is necessary to evaluate the success or failure of the procedure, the quality of life of the patient before and after the procedure, and any complications relating to the procedure. However, patient name, address, social security number, medical records number or other identity information is absent from the medical report. Only the fingerprint information or other biometric information is transmitted and stored in the information center so as to provide a level of anonymity to reports generated from the system.

In other embodiments, additional patient identification information may be provided with the transmitted and stored information. Measures should be taken, however, to ensure anonymity of the patients.

Further patients 24 and 26, for example, are being treated as well and a further biometric data recorder 34 is being used to transmit biometric information of the further patients via an encrypted transmission 36 to the information center 18. The further patients 24 and 26 may be undergoing the same medical procedure as the patients 10, 20 and 22 or may be undergoing an alternative therapy or procedure for comparison purposes. The further patients 24 and 26 may instead be undergoing an entirely different procedure for a different illness or condition. The further biometric data recorder 34 may be of the same type or of a different type as the biometric data recorder 28, and may transmit the same type of biometric data, for example fingerprint data, to the information center or may transmit a different type of biometric data to the information center 18.

Patient information including patient medical status information, medical reports, medical test results and other medical data and information 38 relevant to the medical procedure is transmitted to the information center 18 along with the patient biometric information. The medical data 38 may be in the form of reports completed by the physician or other medical care giver, or may be personal reports by the patient or a family member, for example regarding quality of life issues.

In one example, the medical data 38 is in a computer system, also designated 38, of the medical services provider. The computer system 38 may receive the medical data by direct input by personnel at the doctor's office, for example, or as data from medical devices or data from outside testing services and laboratories. The computer system 38 may have the medical data stored thereon or may serve to send or receive the data from another data storage means, such as a server. The medical data 38 is transmitted via the encrypted transmission means 30 to the information center. The further patients 24 and 26 also have their medical data 40 transmitted to the information center 18 via an encrypted transmission 36. Medical data 38 of several patients and, where applicable, of several steps of the procedure is transmitted to the information center 18, as indicated by the ellipses adjacent the medical data blocks 38 and 40.

The encryption 30 of the transmitted information is important to preserve the privacy of the patient. The biometric data recorder may include means for encrypting and transmitting the encrypted transmission. In one example, a one-way encryption key is hard coded into the biometric data recorder. The one-way encryption key may be generated by a special rule using data from the patient record. In one example of such a rule, the third digit of the patient's birth date and the fourth digit of the procedure date, etc. may be incorporated into an encryption key.

Figure 3:
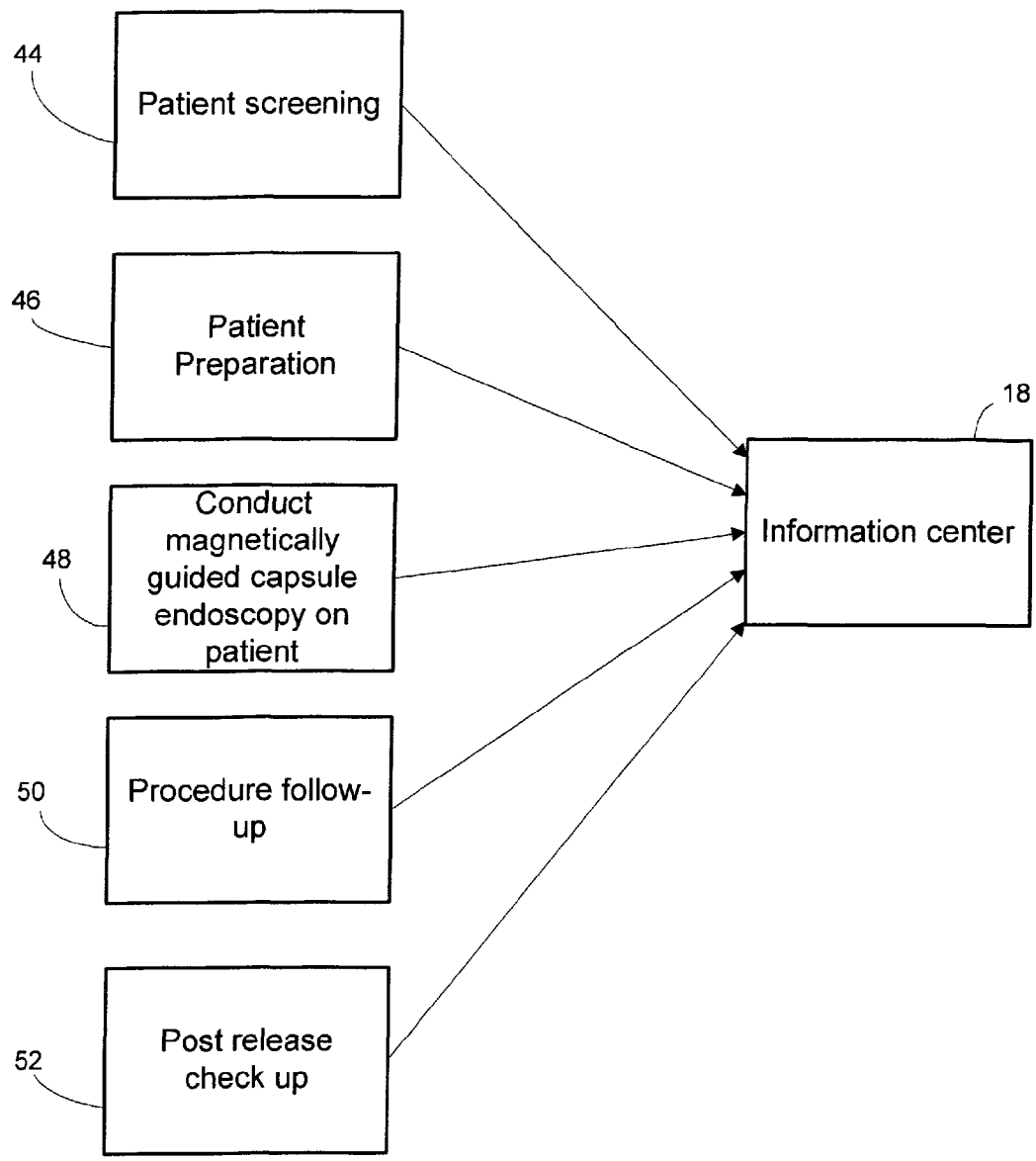
FIG. 3 is a block diagram showing collection of information at various stages of a medical procedure.

In FIG. 3, a medical procedure is being used to treat or diagnose a patient. In this example, the patient initially undergoes a preliminary screening 44. The patient and the patient's medical service provider, for example the patient's doctor, agree to participate in the collection of information program and so send information on the patient's preliminary screening 44 to the information center 18. Following the preliminary screening 44, the patient undergoes preparation 46 for the procedure. Information on the patient preparation 46 may be transmitted to the information center 18. Next, the patient undergoes the procedure, which in the example is a magnetically guided capsule endoscopy (MGCE). The medical service provider forwards information regarding the procedure to the information center 18 using the biometric information of the patient as an identifier. A follow-up 50 or post-procedure examination is performed, and again the patient status information is transmitted to the information center 18. In this example, the patient undergoes a check-up 52 after having been released following the procedure. The patient information of the check-up is also sent to the information center 18.

Each of the steps 44, 46, 48, 50 and 52 may be performed by a different medical services provider, such as by a different doctor or at a different hospital, or may be paid by a different medical payment entity. Nevertheless, the medical data all relates to the same patient and to different steps of the same procedure and is sent to the information center using biometric information of that patient. The result is that the biometric information may be used to group information of that patient so that the medical history of the patient progressing through the procedure may be tracked. The success or failure of the procedure, complications or other information, and a measure of the quality of life of the patient may be made relating to the procedure.

Where the cost information is transmitted to the information center 18 for each of the steps 44, 46, 48, 50 and 52, such as by either the hospital or by the insurance company, the overall cost of the procedure and follow-up care can be determined. An evaluation of quality of life verses cost can be made.

Figure 4:
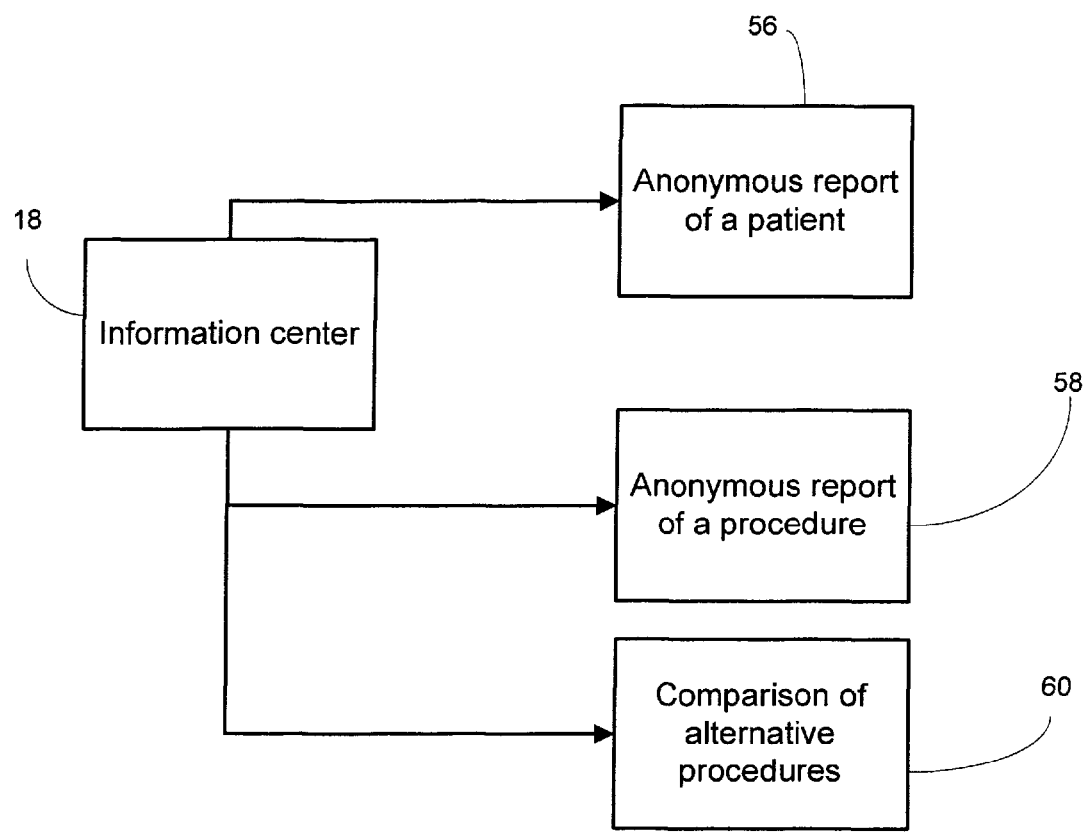
FIG. 4 is a block diagram showing reporting based on information in the information center.

With reference now to FIG. 4, the information center 18 has collected and stored medical data from a number of patients, and preferably from a statistically significant number of patients. The information on each patient may be grouped or otherwise considered together based on the biometric identification information of the patient. The patient is not otherwise identified in the information center so that the identity of the patient cannot be determined. The collected information may be used to prepare an anonymous medical report 56 of the patient.

The collected information in the information center 18 identifies the medical procedure that was performed on each of the patients whose data was collected. It is thereby possible to generate a report 58 with statistical information on the patients who received a given medical procedure, for example a magnetically guided capsule endoscopy procedure. Again, this report is anonymous and does not identify the patients. Further, it is possible to prepare a report 60 that compares the patient's experience with a given medical procedure to the patient experiences with a competing or alternative medical procedure. The comparison 58 and 60 may compare quality of life issues, costs, patient factors such as age or gender, complications, or other factors or issues that may be of interest.

The present method and apparatus enables information to be collected from different medical service providers, such as from different hospitals or different doctors, that might otherwise be recorded under patient chart numbers or other data that does not correlate between the different providers. The present method and apparatus utilizes a patient characteristic such as biometric data, that provides a level of anonymity to the patient compared to using, for example, name and address information, while at the same time providing some assurance that the medical data from the different sources is grouped for each patient.

The present method and apparatus provides statistical information for evidence based medicine (EBM) by providing the possibility to collect and consider many cases and many patients, including patients of different medical service providers and different reimbursement or payment entities. Not only is the present invention capable of providing statistical information for a variety of analyses, but individual cases or patients may be studied anonymously and with a known and measurable accuracy.

The method and apparatus enables successful and beneficial new procedures to rapidly gain a high level of acceptance. An accurate comparison against competing procedures may be rapidly made as the result of the wide range of data collection possible.

To encourage participation in the data collection program for a new procedure, it is envisioned to provide incentives to the patients and/or to the physicians for participating and for transmitting completed reports to the information center.

Thus there is provided a method and apparatus for providing reports of medical procedures includes a biometric data recorder to record and transmit biometric data of a patient, the biometric data being transmitted with a medical report of the medical procedure. The medical report and biometric data are transmitted as an encrypted transmission to an information center for storage. The medical reports of steps in the medical procedure for a patient are linked using the biometric data even if performed by different medical service providers. Medical reports of plural patients undergoing the procedure are stored, linked according to patient using the patient biometric data. Reports generated from the linked data anonymously report a given patient's status following the procedure. Statistical reports are generated on plural patients undergoing the procedure, and competing procedures are compared using the statistical reports.

Although other modifications and changes may be suggested by those skilled in the art, it is the intention of the inventors to embody within the patent warranted hereon all changes and modifications as reasonably and properly come within the scope of their contribution to the art.

We claim:

1. A method of accumulating evidence relating to medical procedures, comprising the steps of:

performing a first step of a medical procedure for a patient to obtain medical data relating to the patient;

obtaining biometric data of the patient using a biometric data recorder;

linking the biometric data of the patient to medical data of the patient obtained by the first step of the medical procedure;

removing patient information from the medical data of the patient of the first step including removing any patient name, patient address, patient social security number, and patient medical records number information from the medical data to provide anonymous medical data of the first step;

transmitting the anonymous medical data of the first step with the biometric data of the patient to an information center as encrypted data via a communication device, the step of transmitting including transmitting the medical data and the biometric data without transmitting any patient name, patient address, patient social security number, and patient medical records number information to the information center;

storing the anonymous medical data of the first step linked to the biometric data of the patient on a data storage device;

performing a second step of the medical procedure for the patient to obtain medical data of the patient of the second step;

linking the biometric data of the patient to the medical data obtained by the second step of the medical procedure;

removing patient information from the medical data of the second step including removing any patient name, patient address, patient social security number, and patient medical records number information from the medical data to provide anonymous medical data;

transmitting the anonymous medical data of the second step with the biometric data of the patient to the information center as encrypted data via a communication device; said step of transmitting the medical data of the second step including transmitting the medical data of the second step with the biometric data of the patient and without transmitting any patient name, patient address, patient social security number, and patient medical records number information;

storing the anonymous medical data of the second step linked to the biometric data of the patient on a data storage device;

performing a medical procedure for a further patient to obtain medical data of the further patient;

obtaining biometric data of the further patient using a biometric data recorder;

linking the biometric data of the further patient to the medical data of the medical procedure performed for the further patient;

removing patient information from the medical data of the further patient including removing any patient name, patient address, patient social security number, and patient medical records number information from the medical data to provide anonymous medical data of the further patient;

transmitting the anonymous medical data of the further patient with the biometric data of the further patient to the information center via a communication device, said step of transmitting the medical data of the further patient including transmitting the medical data of the further patient and the biometric data of the further patient without transmitting any patient name, patient address, patient social security number, and patient medical records number information;

storing the anonymous medical data of the further patient linked to the biometric data of the further patient on a data storage device; and generating a report that is anonymous as to patient identity, the report being generated from data stored in the information center, the report being one of a first report or a second report, the generating of the first report including the substep of combining the anonymous medical data of the first step with the anonymous medical data of the second step of the medical procedure performed on the patient by using the biometric data of the patient to match the data of the first step and the second step, the generating of the second report including the substep of combining the anonymous medical data of the patient with the anonymous medical data of the further patient for a predetermined medical without having access to any patient name, patient address, patient social security number, and patient medical records number information of the patient and the further patient;

wherein said first step of the medical procedure and said second step of the medical procedure are performed by mutually different medical service providers; and further comprising:

providing an incentive to at least one of the medical services provider and the patient for transmitting the medical data to the information center.

2. A method as claimed in claim 1, wherein the medical data of at least one of the first step and the second step and the further patient is forwarded by a medical payment provider.

3. A method as claimed in claim 1, wherein the medical procedure is magnetically guided capsule endoscopy.

4. A method as claimed in claim 1, wherein said steps of transmitting the medical data to the information center transmits an anonymous medical report of the patient along with biometric data of the patient.

* * * * *